(12) United States Patent  
Hill et al.

(10) Patent No.: US 6,195,584 B1
(45) Date of Patent: Feb. 27, 2001

(54) METHOD AND APPARATUS FOR DETERMINING ATRIAL LEAD DISLOCATION

(75) Inventors: Michael R. S. Hill, Minneapolis; Rahul Mehra, Stillwater; Michael F. Hess, Minneapolis; Raylene Pitschneider, Maple Grove, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/303,279

(22) Filed: Apr. 30, 1999

(51) Int. Cl.[7] ........................................... A61N 1/37
(52) U.S. Cl. .................................................. 607/28
(58) Field of Search ............................. 607/8, 9, 27, 28

(56) References Cited

U.S. PATENT DOCUMENTS

| | | |
|---|---|---|
| 4,316,472 | 2/1982 | Mirowski et al. . |
| 4,577,633 | 3/1986 | Berkovits et al. . |
| 4,953,551 | 9/1990 | Mehra et al. . |
| 5,117,824 | 6/1992 | Keimel et al. . |
| 5,163,427 | 11/1992 | Keimel . |
| 5,188,105 | 2/1993 | Keimel . |
| 5,464,431 | 11/1995 | Adams et al. . |
| 5,554,175 | 9/1996 | Alferness . |
| 5,591,215 | 1/1997 | Greenhut et al. . |
| 5,713,932 | 2/1998 | Gillberg et al. . |
| 5,755,736 | 5/1998 | Gillberg et al. . |
| 5,782,889 | * 7/1998 | Hognelid et al. .................... 607/28 |
| 5,817,134 | 10/1998 | Greenhut et al. . |
| 5,861,012 | * 1/1999 | Stroebel ................................ 607/28 |
| 5,865,838 | 2/1999 | Obel et al. . |

FOREIGN PATENT DOCUMENTS

| | | |
|---|---|---|
| 9218198 | 10/1992 | (WO) . |
| 9528987 | 11/1995 | (WO) . |
| 9528988 | 11/1995 | (WO) . |

* cited by examiner

Primary Examiner—Jeffrey R. Jastrzab
(74) Attorney, Agent, or Firm—Reed A. Duthler; Harold R. Patton

(57) ABSTRACT

A method and apparatus for determining the occurrence of a mis-location of an atrial electrode in a cardiac stimulation device having an atrial pulse generator coupled with the atrial electrode and a ventricular sense amplifier coupled to a ventricular electrode. The device paces the atrium in a first pacing mode employing atrial pacing pulses at a first energy level and in a test mode employs higher energy atrial pacing pulses. In the test mode the device measures PR intervals between atrial pacing pulses following sensed ventricular depolarizations and determines that the atrial electrode is mis-located responsive to occurrence of a threshold number of short PR intervals or that the atrial electrode is appropriately located responsive to occurrence of a threshold number of long PR intervals. Operation of the device in the test mode may be pre-conditioned on an absence of atrial tachyarrhythmia.

16 Claims, 5 Drawing Sheets

METHOD AND APPARATUS FOR DETERMINING ATRIAL LEAD DISLOCATION

FIELD OF THE INVENTION

This invention relates to dual chamber cardiac stimulators, e.g. cardiac pacemaker or pacemaker/cardioverter/defibrillator (PCD) systems which rely upon the detection of atrial depolarizations and/or delivery of atrial pacing pulses in the performance of a defined function, and to a method and apparatus for determining the existence of an atrial pace/sense electrode(s) dislocation from an atrial site to a position inferior to the AV node of the heart thereby affecting a function, e.g. providing a false indication of atrial tachyarrhythmia or inappropriate ventricular pacing.

BACKGROUND OF THE INVENTION

Current dual chamber, multi-mode, cardiac pacemakers typically employ atrial and ventricular endocardial pacing leads having one or two distally located pace/sense electrodes that are adapted to be attached in the right atrium and right ventricle, respectively, and operate to sense the atrial and ventricular electrogram (EGM) and deliver pacing pulses to each chamber, depending on the operating mode. Dual chamber demand cardiac pacing is dependent upon the retention of the atrial pace/sense electrode(s) at the atrial site. The dislocation of the atrial pace/sense electrode(s) to a location inferior to the AV node can result in the loss of sensing of the atrial EGM events (principally the P-wave). However, the R-wave of the ventricular EGM as well as other electrical signal peaks of the QRST complex may be readily detected if there is good electrode-tissue contact or may be intermittently detected if the electrode-tissue contact is intermittent. The relatively high gain setting of the atrial sense amplifier necessary to sense the relatively low amplitude P-wave may also contribute to mistaken "sensing" of peaks of the QRST complex and other spurious signals as P-waves. As a result, atrial and ventricular pacing may be inhibited (which may not be undesirable under the circumstances) or become erratic, which could cause a ventricular pacing pulse to be delivered at an undesirable time in the pacing cycle, possibly provoking a tachyarrhythmia. At the least, the benefits of synchronous dual chamber pacing in sustaining a physiologic heart rate and adequate cardiac output would be lost. In addition, atrial pacing pulses may in some cases trigger ventricular depolarizations, possibly inducing ventricular tachyarrhythmias. The same sort of problem may in some cases also occur in response to implant of an atrial electrode low in the right atrium, which may also result in atrial pacing pulses triggering ventricular depolarizations, particularly where higher amplitude pacing pulses are employed, as may be the case during atrial antitachycardia pacing.

In proposed dual chamber PCD systems having the capability of detecting and treating atrial arrhythmias with at least a limited menu of anti-tachyarrhythmia therapies, also referred to as supraventricular arrhythmias and including atrial fibrillation and atrial flutter, the correct diagnosis of the nature of a detected tachyarrhythmia so that an appropriate treatment can be delivered is crucial. Typically, in proposed dual chamber PCD systems, at least both atrial and ventricular pacing and sensing functions are provided in conjunction with tachyarrhythmia detection and anti-tachyarrhythmia therapy delivery in at least one of the chambers. Such dual chamber PCD systems may only provide atrial anti-tachycardia pacing therapies of the types described below or may include atrial cardioversion/defibrillation capabilities as further described below. The failure to deliver the appropriate therapy or the delivery of an inappropriate therapy to treat an apparent atrial tachyarrhythmia can progress to or trigger more serious ventricular tachyarrhythmia. Consequently, a great deal of effort has been undertaken to refine the diagnosis of the tachyarrhythmia and to define the appropriate therapy in response to the diagnosis.

One approach to detection of dislocation or inappropriate location of atrial leads is set forth in U.S. Pat. No. 5,713,932, issued to Gillberg et al. and incorporated herein by reference in its entirety, which discloses a dual chamber cardiac stimulator in which the determination of the occurrence of a dislocation of the atrial pace/sense electrode is effected by applying a test pace pulse to the atrial pace/sense electrode; detecting the immediately following ventricular depolarization from a ventricular sense electrode; measuring the interval between the delivered atrial pace pulse and the detected ventricular depolarization; comparing the measured interval to a threshold AV interval; and determining that the atrial pace/sense electrode is in contact with the right atrium if the measured interval is longer than the threshold AV interval. As disclosed, the determination is effected by: providing a first signal when the measured AV interval exceeds the threshold AV interval and a second signal when the measured AV interval is less than the threshold AV interval; applying a series of M atrial pace pulses to the atrial pace/sense electrode; counting the number of first and second signals provided in response to the series of atrial pace pulses; and determining that the atrial pace/sense electrode is located in the right atrium when a predetermined number of first signals are provided in a series of delivered atrial pace pulses.

SUMMARY OF THE INVENTION

The present invention provides a test method and apparatus for determining atrial lead dislodgment which provides improved performance as compared to the method and apparatus disclosed in the Gillberg et al patent cited above. In addition, the invention will also detect the circumstance in which the location of the lead in the atrium is such that inappropriate ventricular stimulation by atrial pacing pulses may result.

In a preferred embodiment of the present invention, contrary to the Gillberg patent, the test comprises delivery of pulses to the atrial pace/sense electrodes at a higher energy level than atrial pacing pulses delivered during normal operation in standard, dual chamber or atrial pacing modes such as AAI, VDD, DDD, DDI, AAIR, VDDR, DDIR and DDDR modes. The purpose of the increased amplitude test pulses is to increase the likelihood that the delivered test pulses will cause depolarization of adjacent ventricular heart tissue if the atrial lead is actually dislodged or is located in the atrium in a position in which ventricular stimulation is possible.

As noted in the Gillberg et al. patent, an atrial lead dislodged into the ventricle may only make intermittent contact with the ventricular tissue. To deal with this problem, the Gillberg patent requires that only some of the delivered test pulses trigger short measured AV intervals, under the assumption that at those times when the atrial electrode is in contact with ventricular tissue during delivery of the test pulses, the pulses will be effective to capture the heart. However the present invention recognizes that a dislodged lead is located at a location which was not chosen by the physician and at which pacing and sensing thresholds were not taken. While the relatively low sensing threshold likely to be in effect for the atrial sense amplifier makes it relatively likely that ventricular depolarizations will be sensed by the atrial sense amplifier, even in cases in which the dislocated lead is at a stable location in the ventricle, the ventricular pacing threshold may be greater than the programmed atrial pacing pulse amplitude. In a device as in the Gillberg et al. patent, this may lead to the unfortunate situation in which the displaced lead functions to sense ventricular depolarizations without its dislodgment being detected.

In preferred embodiments of the present invention, again contrary to the teaching of the Gillberg et al. patent, instead of being delivered in response to a determination that an atrial tachyarrhythmia is likely underway, the test pulses delivered to the atrial pace/sense electrodes are inhibited if an atrial tachyarrhythmia is underway and are delivered only if the patient appears to be in normal sinus rhythm. While this feature prevents the test pulses from being employed to confirm a provisional diagnosis of atrial tachyarrhythmia, it reflects the fact that atrial-ventricular conduction times may be quite variable during atrial fibrillation and that determining the correspondence of a delivered test pulse to a sensed ventricular depolarization may thus be difficult. In these embodiments of the invention, confirmation of lead dislodgment or inappropriate lead position in the atrium may be employed to disable atrial anti-tachyarrhythmia therapies and/or atrial or dual chamber pacing modes until the device is reprogrammed by the physician. The increased accuracy of the determination of lead displacement or inappropriate lead location in the atrium provided by assuring that the test is conducted only if atrial tachyarrhythmias are not underway is particularly desirable in this context. The result of a determination of displacement or inappropriate location preferably extends until the next time the patient is treated by a physician. In these embodiments of the invention, detection of an atrial tachyarrhythmia during the test terminates the test, and anti-atrial tachyarrhythmia therapy is delivered.

In some embodiments of the invention, a defined number of beats is specified for the test and the test continues until either the defined number of beats has occurred or a threshold number of short measured A–V intervals following delivered test pulses has been reached. In alternative embodiments, the test may be terminated in response to a threshold number of long A–V intervals following delivered test pulses has been reached. The increased accuracy of the test method again is especially beneficial in these embodiments, as it allows earlier test termination while still allowing accurate detection of displacement. Early test termination in turn is valuable to minimize energy expenditures associated with the higher amplitude test pulses.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
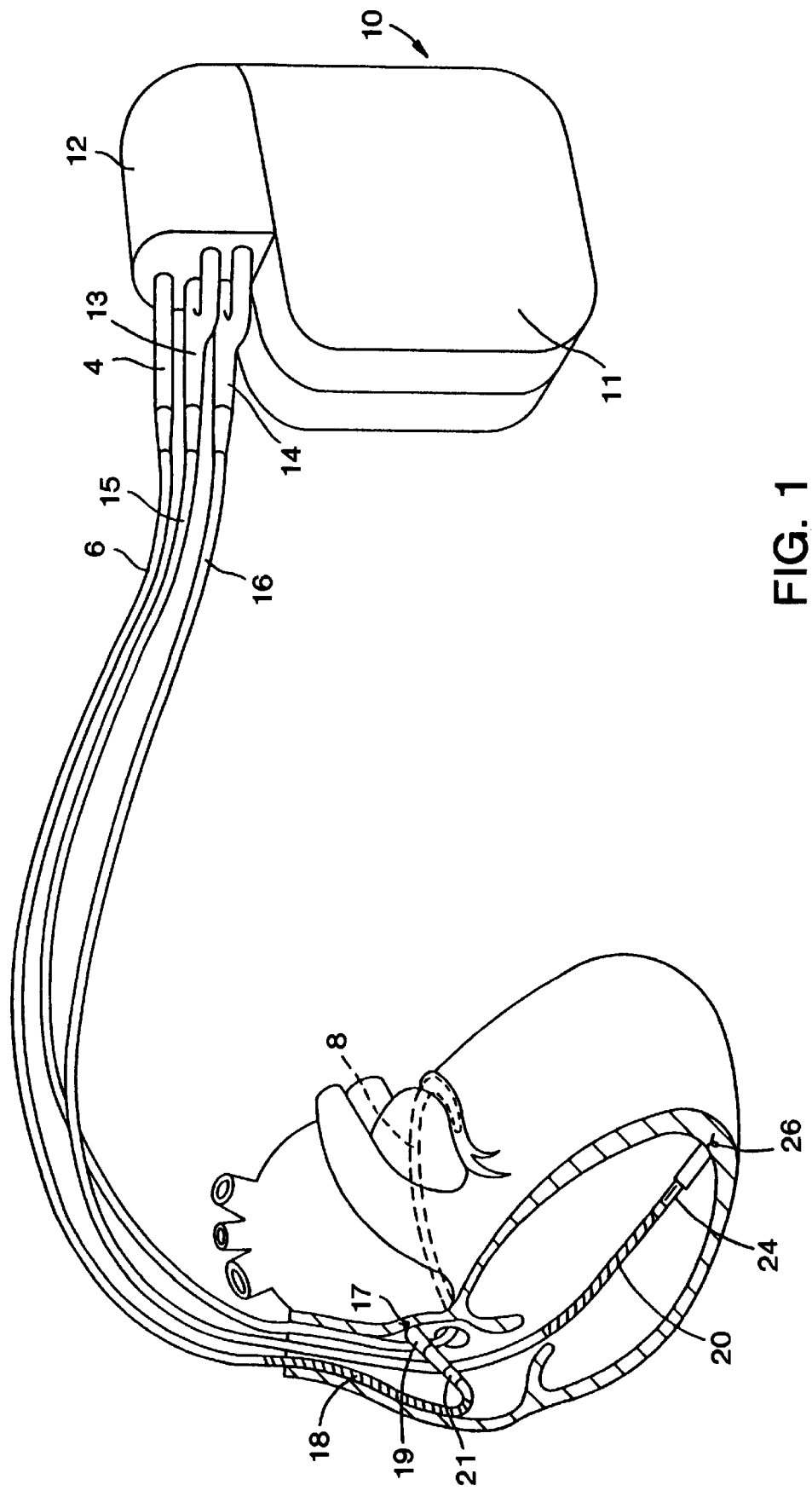
FIG. 1 illustrates a first embodiment of an implantable PCD system of a type appropriate for use in practicing the present invention, in conjunction with a human heart wherein the atrial pace/sense electrodes of an atrial lead are properly located in the right atrium.
Figure 2:
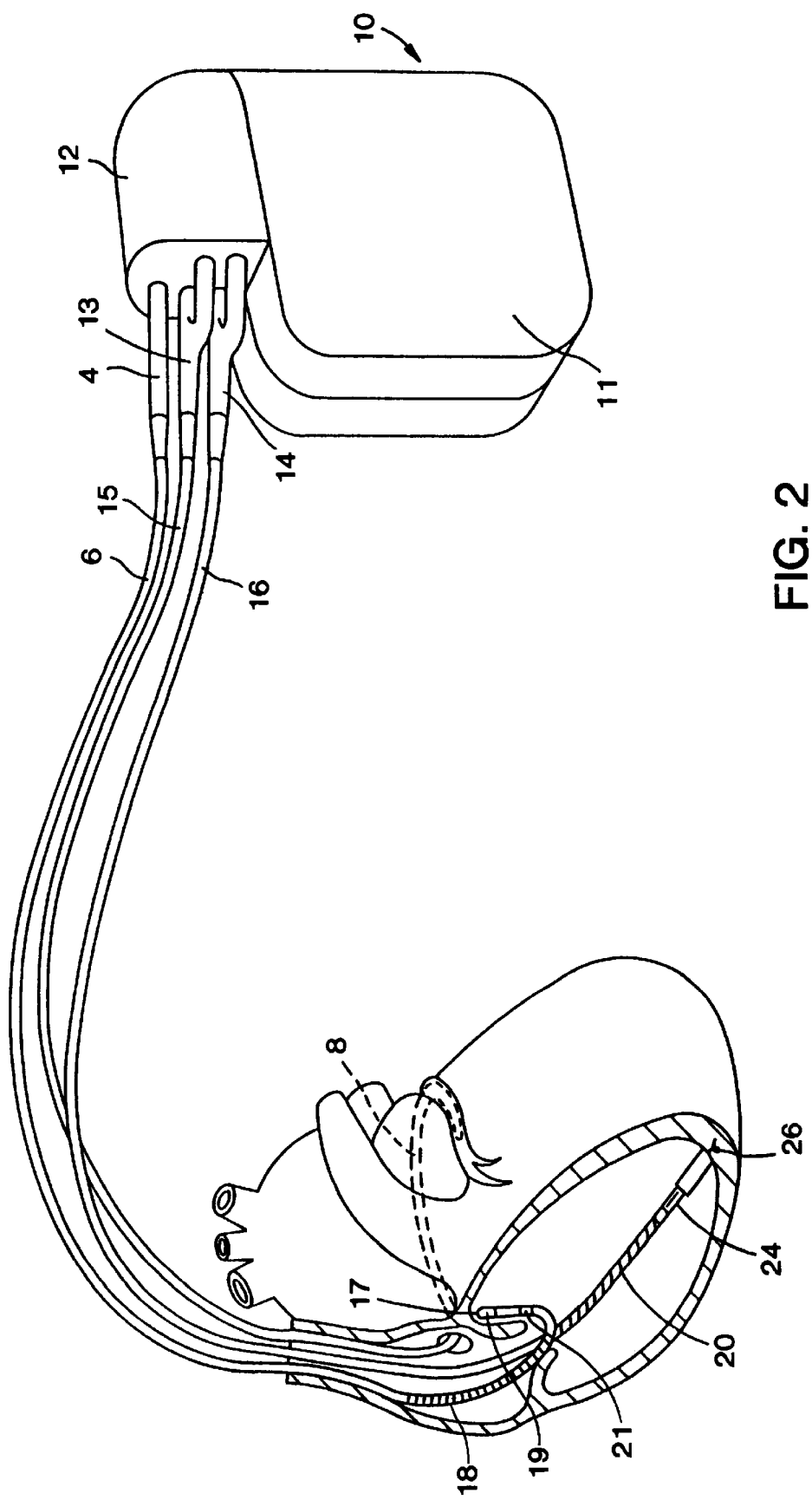
FIG. 2 illustrates the implantable PCD system of FIG. 1 in conjunction with a human heart wherein the atrial pace/sense electrodes of an atrial lead are dislodged into the right ventricle.
Figure 3:
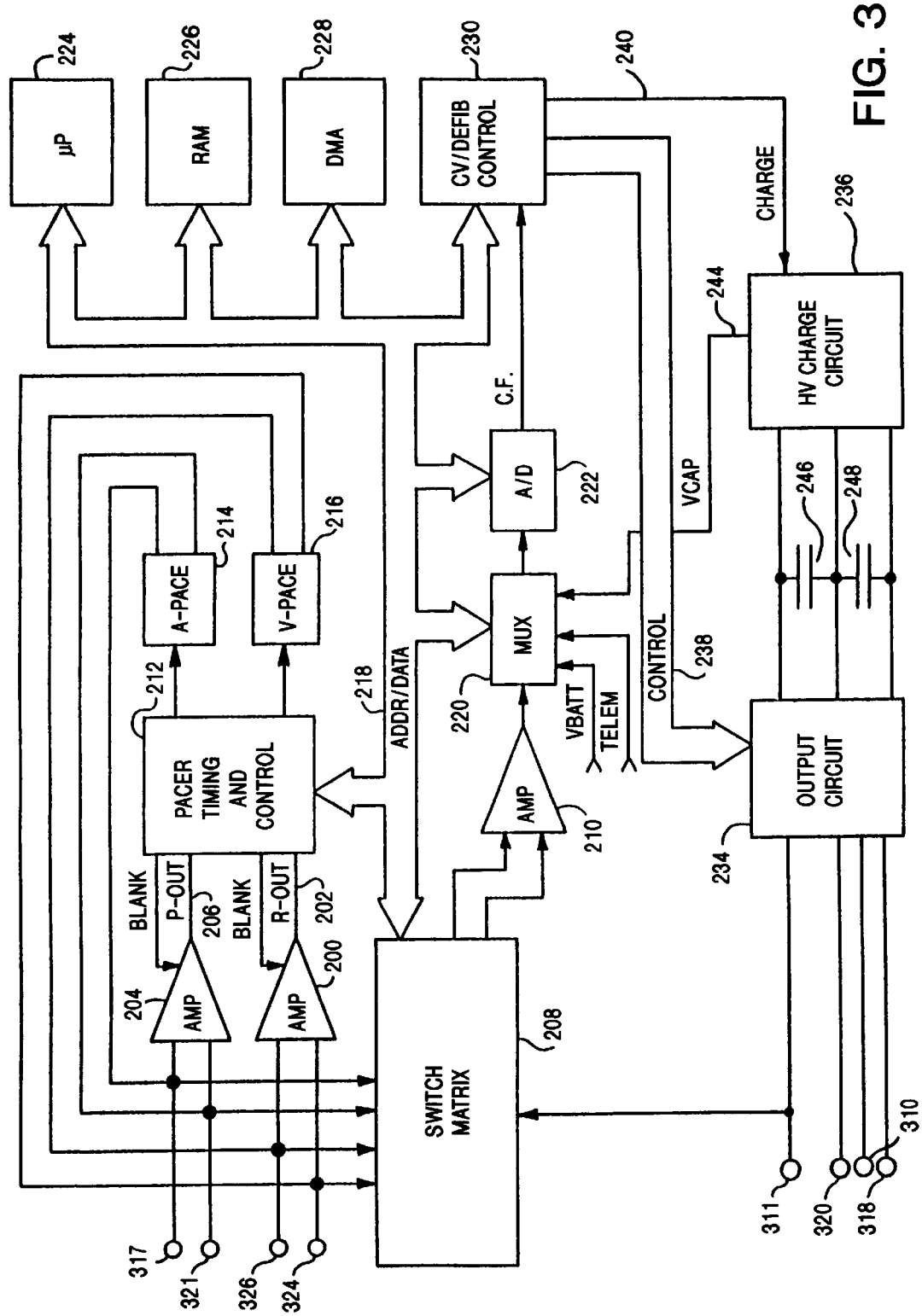
FIG. 3 illustrates a functional schematic diagram of an implantable PCD in which the invention may be practiced.
Figure 4:
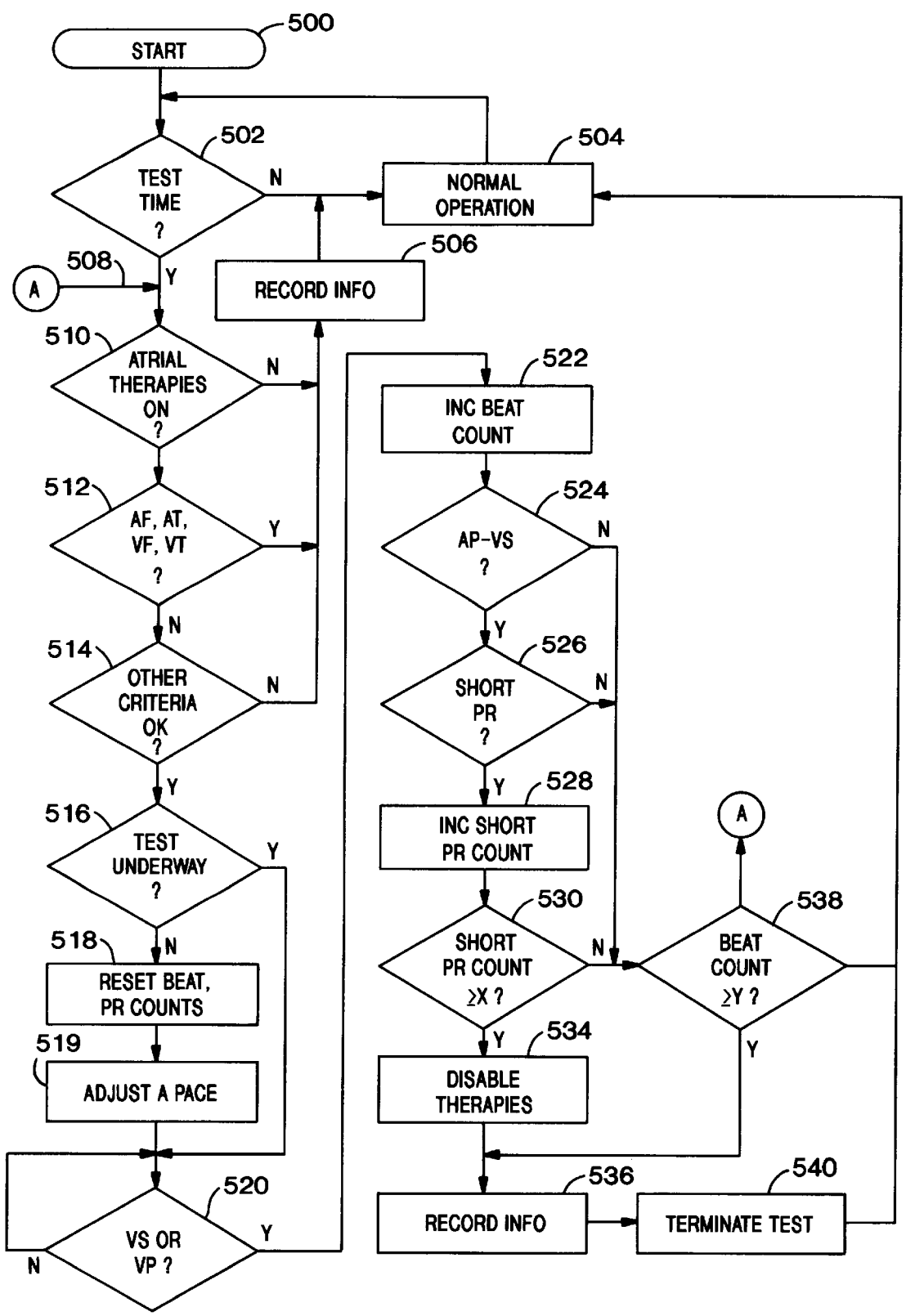
FIGS. 4 and 5 are flowcharts illustrating the operation of a device incorporation the present invention.
Figure 5:
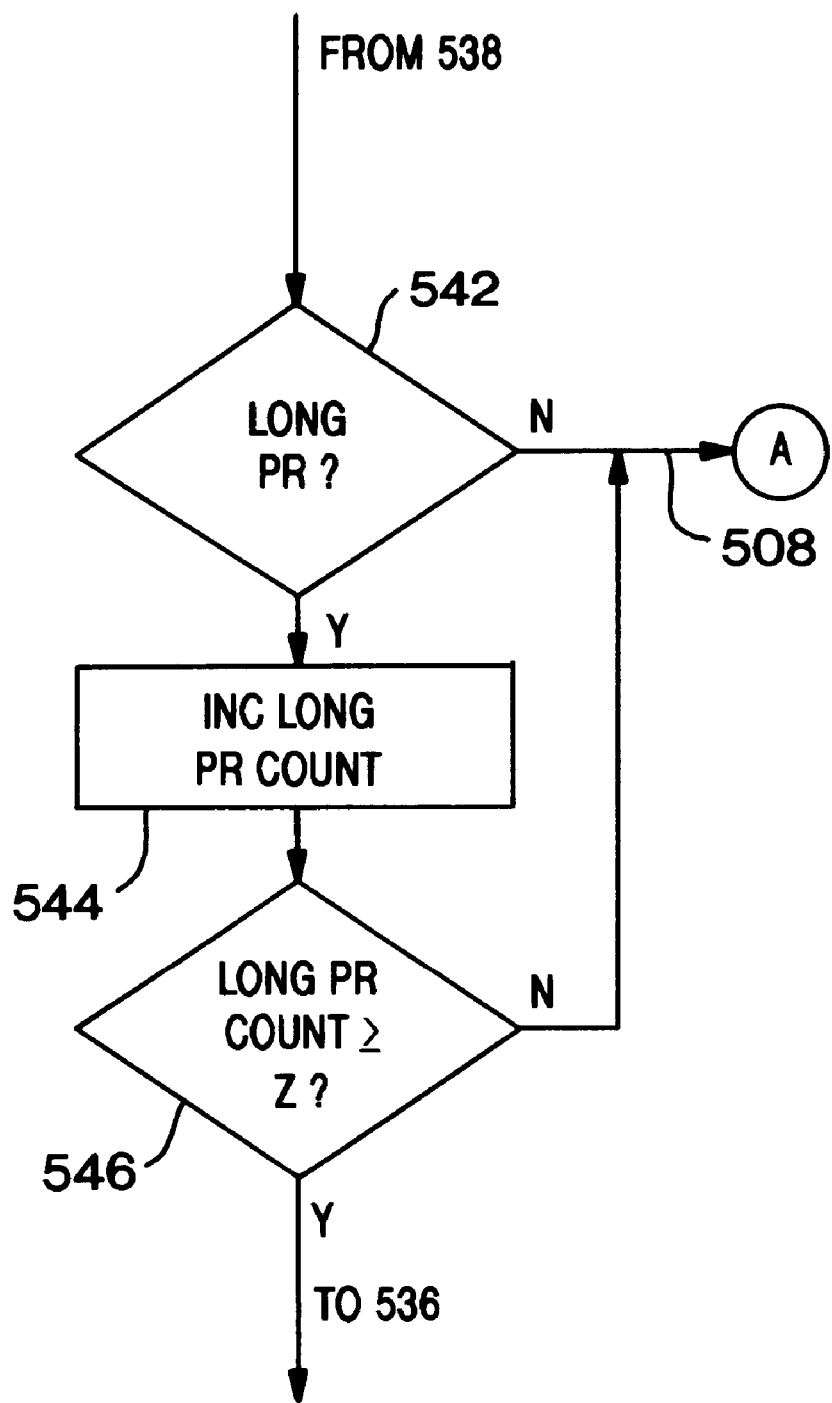

FIGS. 1–3 illustrate a PCD implantable pulse generator (IPG) 10 and lead set of a type in which the present invention may be implemented. FIG. 3 is a functional schematic diagram of the circuitry of a dual chamber, implantable PCD IPG 10 in which the present invention may usefully be practiced. Certain of the pace/sense and cardioversion/defibrillation functions and associated leads and electrodes may be disabled or not provided to configure the PCD system to operate in accordance with the preferred embodiments and variations described below. FIG. 3 should be taken as exemplary of the circuitry of the type of single chamber or dual chamber PCD IPG in which the invention may be embodied, and not as limiting, as it is believed that the invention may usefully be practiced in a wide variety of device implementations, as long as the operating mode or configuration involves use of an atrial sensing lead and atrial sense functions that may be adversely affected by dislocation of the atrial pace/sense electrode(s) from the intended site in the right atrium. In this regard, the present invention may have application in any dual chamber pacemaker without the capability of determining the existence of and responding to a tachyarrhythmia. The flow charts of FIGS. 4–6 illustrate these possible applications and embodiments of the present invention.

Turning first to the description of the leads illustrated in FIGS. 1 and 2, the right ventricular (RV) lead includes an elongated insulated lead body 16, carrying three concentric coiled wire conductors, separated from one another by tubular insulated sheaths. Located adjacent the distal end of the RV lead are a ring electrode 24, an extendible helix electrode 26, mounted retractably within an insulated electrode head 28, and an elongated, exposed coil, cardioversion/defibrillation electrode 20. Each of the electrodes is coupled to one of the coiled conductors within the lead body 16. Electrodes 24 and 26 are employed for cardiac pacing and for sensing ventricular depolarizations. At the proximal end of the lead is a bifurcated connector 14 which carries three electrical connectors, each coupled to one of the coiled conductors, that are fitted into a high voltage and a low voltage receptacle of the connector block assembly 12 of the PCD IPG 10. The RV cardioversion/defibrillation electrode 20 may be fabricated from platinum, platinum alloy or other materials known to be usable in implantable defibrillation electrodes and may be about 5 cm in length.

The right atrium-superior vena cava (RA/SVC) lead includes an elongated insulated lead body 15, carrying three concentric coiled conductors, separated from one another by tubular insulated sheaths, corresponding to the structure of the ventricular lead. Located adjacent the J-shaped distal end of the lead are a ring electrode 21 and an extendible helix electrode 17, mounted retractably within an insulated electrode head 19. Each of these pace/sense electrodes 17, 21 is coupled to one of the coiled conductors within the lead body 15. Pace/sense electrodes 17 and 21 are employed for atrial pacing and for sensing atrial depolarizations. An elongated RA/SVC cardioversion/defibrillation electrode 23 is optionally provided, extending proximally with respect to ring pace/sense electrode 21 and is coupled to the third conductor within the RA/SVC lead body 15. Electrode 23 preferably is 10 cm in length or greater and is intended to extend from the SVC toward the tricuspid valve in the normal fixation location depicted in FIG. 1. A bifurcated connector 13 is located at the proximal end of RA/SVC lead body 15 and carries three electrical connectors, each coupled to one of the coiled conductors, that are inserted into a high voltage receptacle and a low voltage receptacle of the connector block assembly 12 of the PCD IPG 10.

The coronary sinus (CS) lead includes an elongated insulated lead body 6, carrying one coiled conductor, coupled to an elongated, exposed coil, cardioversion/defibrillation CS electrode 8. Electrode 8, illustrated in broken outline, is located within the coronary sinus and great vein of the heart. At the proximal end of the lead is a connector plug 4 which carries an electrical connector, coupled to the coiled conductor. The coronary sinus/great vein electrode 8 may be about 5 cm in length.

A PCD implantable pulse generator (IPG) 10 is shown in combination with the leads, with the lead connectors 4, 13 and 14 inserted into the receptacles of the connector block assemblies 12. Optionally, insulation of the outward facing portion of the housing 11 of the PCD IPG 10 may be provided using a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing or can 11 optionally serves as a subcutaneous defibrillation "CAN" electrode, used to defibrillate either the atria or ventricles. Other lead configurations and electrode locations may of course be substituted for the lead set illustrated. For example, atrial defibrillation and sensing electrodes might be added to either the coronary sinus lead or the right ventricular lead instead of being located on a separate atrial lead, allowing for a two-lead system.

In FIG. 1, the atrial pace/sense electrodes 17, 21 are shown lodged into the right atrial appendage in the intended position of fixation. The distal tip, pace/sense electrode 17 in the illustrated case is formed of an active fixation helix that is screwed into the myocardium. It will be understood that the fixation mechanism may be a passive fixation mechanism as described above. At times, the fixation mechanism fails to retain the distal tip pace/sense electrode in the intended position, and, if the patient is not pacemaker dependent, the loss of atrial contact may not be noticeable to the patient. FIG. 2 illustrates the slippage of the RA/SVC lead further into the right ventricle. The distal tip and ring pace/sense electrodes may bear against the right ventricular endocardial surface and make continuous or intermittent contact. In this dislocated position, the ability to detect atrial depolarizations between the atrial pace/sense electrodes 17, 21 may be lost due to the location below the AV node of the heart and the relatively low amplitude P-wave in that location. However, the R-wave of ventricular depolarizations as well as other signals may be readily detected if there is good electrode-tissue contact or may be intermittently detected if the electrode-tissue contact is intermittent. The relatively high gain of the atrial sense amplifier in PCD IPG 10 may also contribute to mistaken sensing of other spurious signals as P-waves.

FIG. 3 is a functional schematic diagram of an implantable PCD IPG in which the present invention may usefully be practiced. This diagram should be taken as exemplary and inclusive of the major components of the type of device in which the invention may be embodied, and not as limiting, as it is believed that the invention may usefully be practiced in a wide variety of device implementations, including devices providing therapies for treating atrial tachyarrhythmias instead of or in addition to ventricular tachyarrhythmias, cardioverters and defibrillators which do not provide anti-tachycardia pacing therapies, anti-tachycardia pacers which do not provide cardioversion or defibrillation therapies, and devices which deliver different forms of anti-tachyarrhythmia therapies such as nerve stimulation or drug administration. Moreover, the invention may be practiced in a dual chamber pacemaker employing atrial and ventricular sense electrode(s) and having only bradycardia sensing, determination and pacing capabilities in one or both heart chambers.

The PCD IPG of FIG. 3 is intended to be provided with a lead system including pace/sense electrodes, which may be as illustrated in FIGS. 1 and 2, although alternative lead systems may of course be used with it, as long as an atrial lead and atrial pace/sense electrode is in the system. If the electrode configuration of FIGS. 1 and 2 is employed, the correspondence of the illustrated electrodes to the illustrated connector terminals is as follows.

Terminal 311 is adapted to be coupled with CAN electrode 11 when the CAN electrode 11 is used in the system. High voltage terminals 318, 320 and 310 are adapted to be coupled with RA/SVC cardioversion/defibrillation electrode 18, RV cardioversion/defibrillation electrode 20, and CS cardioversion/defibrillation electrode 8, respectively. Terminals 311, 318, 320 and 310 are coupled to the outputs of the high voltage output circuit 234. In alternative PCD IPG embodiments of the invention, only two or three high voltage terminals and associated electrodes may be provided. In other pacing only embodiments, the high voltage terminals and associated leads and illustrated components of FIG. 3 (described below) may be eliminated from the system.

Low voltage terminals 324 and 326 are adapted to be coupled with RV pace/sense electrodes 24 and 26, and are used for conducting ventricular sense events and pace pulses from and to the right ventricle. Low voltage terminals 317 and 321 are adapted to be coupled with RA pace/sense electrodes 17 and 21, and are used for conducting atrial sense events and pace pulses from and to the right atrium (when the atrial lead is in the normal position of FIG. 1). Terminals 324 and 326 are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between terminals 324 and 326 exceeds the programmed sensing threshold. Terminals 317 and 321 are coupled to the P-wave amplifier 204 which preferably also takes the form of an automatic gain controlled amplifier providing an adjustable sensing threshold as a function of the measured P-wave amplitude. A signal is generated on P-out line 206 whenever the signal sensed between electrodes 317 and 321 exceeds the programmed sensing threshold. The general operation of the R-wave and P-wave amplifiers 200 and 204 may correspond to that disclosed in U.S. Pat. No. 5,117,824, by Keimel, et al., incorporated herein by reference in its entirety. In any of the various embodiments of the present invention, at least the atrial and ventricular pace/sense electrode(s) and sense amplifiers 204, 200 must be present.

Switch matrix 208 is used to select which of the available terminals and associated electrodes are coupled to wide band (0.5–200 Hz) amplifier 210 for use in digital EGM signal analysis. Selection of electrodes is controlled by the microprocessor 224 via data/address bus 218, which selections may be varied as desired. Signals from the electrodes selected for coupling to bandpass amplifier 210 are provided to multiplexor 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

The remainder of the IPG circuitry is dedicated to the diagnosis of a bradycardia or tachyarrhythmia and the provision of cardiac pacing, cardioversion and defibrillation therapies, and, for purposes of the present invention may correspond to circuitry known in the prior art, as well as the performance of the functions and determinations of the various embodiments of the present invention illustrated in FIGS. 4–7.

The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art. Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by R-OUT and P-OUT signals on lines 202 and 206, and in accordance with the selected pacing mode, on time-out trigger generation of pacing pulses by pacer output circuits 214 and 216. The escape interval counters are also reset on generation of pacing pulses, and thereby control the basic timing of cardiac pacing functions, including anti-tachyarrhythmia pacing.

The durations of the intervals defined by the escape interval counters are determined by microprocessor 224, via data/address bus 218. The value of the count present in the escape interval counters when reset by sensed R-waves and P-waves may be used to measure the durations of V—V intervals, A—A intervals, AV intervals and V-A intervals, which measurements are stored in memory 226 and used in conjunction with the present invention to diagnose the occurrence of a variety of tachyarrhythmias and the dislocation of the atrial pace/sense electrode(s), as discussed in more detail below.

Microprocessor 224 operates as an interrupt driven device under control of programming stored in the read only memory therein and/or random access memory 226, and is responsive to interrupts from pacer timing/control circuitry 212 received via data/address bus 218 and corresponding to the occurrences of P-OUT and R-OUT signals generated by sense amplifiers 204 and 200 and corresponding to the generation of A-PACE and V-PACE cardiac pacing pulses by pacing pulse generators 214 and 216. Any necessary mathematical calculations to be performed by microprocessor 224 and any updating of the values or intervals controlled by pacer timing/control circuitry 212 take place following such interrupts. A portion of the memory 226 (FIG. 4) may be configured as a plurality of recirculating buffers, capable of holding several series of measured V—V, V–A, A—A and A–V intervals, which may be analyzed in response to the occurrence of a predetermined count of pace or sense interrupts to determine whether the patient's heart is presently exhibiting atrial or ventricular tachyarrhythmia. The intervals may be compared with various threshold intervals employed in tachyarrhythmia analysis and determination and in the practice of the present invention as described in detail below. The threshold intervals may be programmed into memory or calculated by the microprocessor and stored in memory for use in such determinations. Also counters may be configured to store counts of events and the results of comparisons during the determination of the tachyarrhythmia and the location of the atrial pace/sense electrodes The arrhythmia detection method of the present invention may include any prior art tachyarrhythmia detection algorithms and in particular ma correspond to the tachyarrhythmia detection algorithms employed in U.S. Pat. No. 5,755,736 issued to Gillberg et al., incorporated herein by reference in its entirety. Alternative examples of algorithms for detecting and identifying atrial and ventricular tachyarrhythmias which may usefully employed in a device embodying the invention are set forth in U.S. Pat. No. 5,554,175, issued to Alferness, U.S. Pat. No. 5,827,197, issued to Bocek et al., U.S. Pat. No. 5,464,431, issued to Adams et al., U.S. Pat. No. 5,865,838, issued to Obel et al, U.S. Pat. No. 5,817,134, issued to Greenhut et al. and U.S. Pat. No. 5,591,215, issued to Greenhut, all incorporated herein by reference in their entireties.

In such complex arrhythmia determination and discrimination systems as described above, it is assumed that the atrial pace/sense electrodes are fixed in the right atrial heart chamber superior to the AV node. For example, such a presumption prevails in the method of distinguishing 1:1 sinus tachycardia from 1:1 paroxysmal tachycardia proposed by Arzbaecher et al. as described above. In the vast majority of implantations, unipolar or bipolar atrial pace/sense electrodes are introduced into the right atrium and typically lodged in the right atrial appendage or wall where they remain in place. Fixation of the electrode(s) is effected either with a passive fixation mechanism, e.g. soft pliant tines that engage in the trabecular structure of the right atrial appendage, or an active fixation mechanism, e.g. a helical coil distal tip electrode that is screwed into a relatively thick portion of the right atrial wall. Despite the efforts to maintain fixation, the atrial pace/sense electrode(s) can, on rare occasion, become dislodged and migrate through the tricuspid valve into the right ventricle at some time after implantation and medical discharge of the patient.

In such a dislocation position, the electrogram signals that are processed as atrial sense events may actually reflect the activity of the atria and the ventricles or just the ventricles or reflect oversensing due to intermittent contact of the electrode(s) with the endocardium and the gain setting of the atrial sense amplifier. The resulting sequences of event patterns derived from the ventricular and atrial sense amplifiers can be erroneously interpreted by the algorithm as representing an atrial tachyarrhythmia, and the device can trigger delivery of a programmed therapy for that tachyarrhythmia.

In the event that an atrial or ventricular tachycardia is so determined, and an antitachycardia pacing regimen is programmed, appropriate timing intervals for controlling generation of anti-tachycardia pacing therapies are loaded from microprocessor 224 into the pacer timing and control circuitry 212, to control the operation of the escape interval counters therein and to define refractory periods during which detection of R-waves and P-waves is ineffective to restart the escape interval counters. Circuitry may be used for controlling the timing and generation of anti-tachycardia pacing pulses as described in U.S. Pat. No. 4,577,633, issued to Berkovits et al., incorporated herein by reference.

In the event that generation of a cardioversion or defibrillation shock is programmed, microprocessor 224 employs an escape interval counter to control timing of such cardioversion and defibrillation shocks, as well as associated refractory periods. In response to the detection of atrial or ventricular fibrillation or tachyarrhythmia necessitating a cardioversion shock, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexor 220 and, in response to reaching a predetermined value set by microprocessor 224, results in generation of a logic signal on Cap Full (CF) line 254, terminating charging. Thereafter, timing of the delivery of the defibrillation or cardioversion shock is controlled by pacer timing/control circuitry 212. Following delivery of the fibrillation or tachycardia therapy, the microprocessor 224 then returns device operation to bradycardia cardiac pacing and awaits the next successive interrupt due to pacing or the occurrence of a sensed atrial or ventricular depolarization.

One embodiment of an appropriate system for delivery and synchronization of ventricular cardioversion and defibrillation shocks and for controlling the timing functions related to them is disclosed in more detail in commonly assigned U.S. Pat. No. 5,188,105 by Keimel, and incorporated herein by reference in its entirety. If atrial cardioversion/defibrillation capabilities are included in the IPG, appropriate systems for delivery and synchronization of atrial cardioversion and defibrillation therapies and for controlling the timing functions related to them may be found in PCT Patent Application No. WO92/18198 by Adams et al., and in U.S. Pat. No. 4,316,472 by Mirowski et al., both incorporated herein by reference in their entireties.

In addition, high frequency pacing pulse bursts may be delivered to the atrial or ventricular pace/sense electrode pairs 19, 21 or 24, 26 to terminate atrial or ventricular tachyarrhythmias, as described in PCT Patent Publication No. WO95/28987, filed by Duffin et al., and PCT Patent Publication No. WO95/28988, filed by Mehra et al., both incorporated herein by reference in their entireties.

In the illustrated PCD IPG of FIG. 3, delivery of the cardioversion or defibrillation shocks is accomplished by output circuit 234, under control of control circuitry 230 via control bus 238. Output circuit 234 determines whether a monophasic or biphasic pulse is delivered, whether the housing 11 serves as cathode or anode, and which electrodes are involved in delivery of the pulse. Examples of circuitry which may be used to control delivery of monophasic or biphasic cardioversion shocks are set forth in commonly assigned U.S. Pat. Nos. 5,163,427 issued to Keimel, and 4,953,551, issued to Mehra et al., respectively, both incorporated herein by reference.

In modem PCD IPGs, the particular therapies are programmed into memory ahead of time by the physician, and a menu of such therapies is typically provided. For example, on initial detection of an atrial or ventricular tachycardia, an anti-tachycardia pacing therapy may be selected and delivered to the chamber in which the tachycardia is diagnosed or to both chambers. On re-detection of tachycardia, a more aggressive anti-tachycardia pacing therapy may be scheduled. If repeated attempts at anti-tachycardia pacing therapies fail, a higher energy cardioversion shock may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion shocks if the rate of the detected tachycardia is above or accelerates above a preset threshold.

In the event that fibrillation is identified either initially or through progression from a tachycardia, a high frequency burst of pacing pulses may be employed as the initial attempted therapy. Subsequent therapies may be delivery of high amplitude defibrillation shocks, typically in excess of 5 joules. Lower energy levels may be employed for synchronized cardioversion shocks delivered in synchronization with an R-wave. It is envisioned that the amplitude of the defibrillation shock may be incremented in response to failure of an initial shock or shocks to terminate fibrillation.

These various types of anti-tachyarrhythmia therapies that may be employed in the PCD IPG system are merely illustrative and do not affect the present invention. However, it is recognized that the delivery of an inappropriate therapy in response to an erroneous determination of the nature of an atrial or ventricular tachyarrhythmia may have serious consequences to the patient. As described above, dislocation of the atrial pace/sense electrode(s) into the ventricle or tricuspid valve can cause such an erroneous determination due to the delivery of P-OUT signals in rapid succession in response to a variety of signal sources. The present invention is directed in this context and in other contexts to making a determination as to when an atrial lead is dislocated such that the atrial pace/sense electrode is positioned in the ventricle (e.g. the RA/SVC lead position depicted in FIG. 2), and the purported atrial sense events (the P-OUT signals of sense amplifier 204 of FIG. 3, for example) are not to be relied on or may be used to bias a determination. The electrode dislocation determination may be made in an atrial pace test sequence initiated at a given time of day or by a programmed command, subject to a determination that neither atrial nor ventricular tachyarrhythmias are underway. The test sequences and the determinations made from the test sequences are illustrated in the flowcharts which follow.

FIG. 4 is a functional flow chart illustrating the overall operation of the device as it performs testing to determine whether the atrial lead is mis-located, whether due to dislocation of the atrial lead into the ventricle or inappropriate location of the lead in the atrium. After initialization at 500, the device operates in its normal pacing mode at 504 until occurrence of a scheduled test time. A time for the lead dislocation test may be scheduled on a daily, weekly or monthly basis, but preferably is scheduled on a daily basis. If the test time has been reached, the device checks at 510 to determine whether atrial anti-tachyarrhythmia therapies are presently enabled. If not, the device returns to normal operation at 504, optionally recording information as to the reason for test determination at 506. If atrial antitachyarrhythmia therapies are enabled, the device then checks at 512 to determine whether an atrial or ventricular tachyarrhythmia, such as atrial fibrillation, atrial tachycardia, ventricular fibrillation or ventricular tachycardia is currently underway. In the presence of any of these types of tachyarrhythmias, the test is aborted, information as to the reason for aborting the test is optionally recorded at 506, and the device returns to normal operation at 504 which, in this case, presumably would include the possibility of an atrial or ventricular anti-tachyarrhythmia therapy.

In the event that atrial and ventricular tachyarrhythmias are not underway, the device then checks to see if any other features are active which preclude operation of the test. Such features may include, for example, an open read switch enabling telemetry transmission, a telemetry transmission tour from the device presently underway, a mode switch operation in which the device changes from one pacing mode to another, e.g., from an atrial synchronous to non-atrial synchronized pacing mode, or the operation of a physician requested temporary therapy of any sort.

Assuming that all conditions for initiation of the test are appropriate, the device confirms that the test is not presently underway at 516 and initiates the test at 518 and 519. As noted above, a defined maximum number of ventricular depolarizations or heartbeats are allowed to occur during the test. At 518 a beat counter is reset to zero, initializing the count of heartbeats occurring during the test. Similarly, as noted above, the test is terminated in response to detection of a preset number of short atrial paced—ventricular sense intervals (PR intervals). At 518 a count of short PR intervals is reset to zero as well. At 519, the parameters of the atrial pacing pulses to be delivered to the test are adjusted. Typically, this involves increasing the amplitude and/or width of the pulse as compared to normal bradycardia pacing. In addition, the rate of delivery of atrial pacing pulses may be increased in order to overdrive the underlying intrinsic heart rhythm and assure that atrial pacing pulses are actually delivered during the test, as described in the above cited '932 Gillberg et al. patent.

On each occurrence of a ventricular sensed event or delivered ventricle pacing pulse at 520, the device increments the beat counter at 522 and checks at 524 to determine whether the preceding ventricular event ended an atrial pace—ventricular sense sequence. If so, the device compares the interval between the atrial pace and the ventricular sense (PR interval) to a threshold interval, for example 30 to 100 milliseconds. If the PR interval is less than this threshold interval, the count of short PR intervals is incremented at 522 and the incremented count is compared to a programmed number "X", which may be, for example, 4 to 10. If the short PR interval count exceeds this value, atrial anti-tachyarrhythmia therapies are disabled at 534 and information concerning the outcome of the test and the reason for disabling the atrial anti-arrhythmia therapies is recorded at 536. The test is then terminated at 540 and the device returns to a normal operation at 504. Subsequent scheduled atrial lead dislodgment tests may optionally be canceled at this point, or subsequent tests may be performed in order to gather additional information to assist the physician in making a diagnosis.

In the event that the short PR interval count is less than the programmed number "X" at 530, the device checks at 538 to determine whether the beat count exceeds the predetermined number of heartbeats allowed for the test sequence, which may be, for example, 10 to 100 beats. If so, information as to the outcome of the test, which in this case would indicate that the atrial lead is not dislodged, is stored at 536 and the test is terminated at 540. The device then awaits occurrence of the next scheduled test time at 502.

In the event that the short PR count is less than "X" and the beat count is less than "Y", the device returns to point A (508) of the flow chart and again determines whether the conditions for initiating the test still persist. Basically, at any time during the test, if the conditions for initiating the test cease to be met, the test is terminated, and the reason for termination of the test is stored at 506, and the device awaits occurrence of the next subsequent scheduled test time.

FIG. 5 illustrates an alternative embodiment of a method of operation of a device according to the present invention. the flow chart of FIG. 5 represents a portion of the flow chart of FIG. 4, modified to allow for early termination of the test sequence in response to the occurrence of a predetermined number of measured PR intervals greater than a defined value. In this embodiment, on initiation of the test sequence, a separate count of long PR intervals is provided, which may be intervals either that are greater than a threshold interval duration employed for recognizing short PR intervals, or may be intervals which are greater than a second threshold value, which value is greater than the threshold value for determination of short PR intervals.

The flow chart of FIG. 5 is entered in response to a determination at 538 that the beat count is less than the defined number "Y" of beats allowed for the test. If so, the device checks at 542 to determine whether the preceding heartbeat sequence ended with an atrial pace-ventricular sense sequence and whether the associated PR interval was greater than a defined threshold duration, which may be equal to or greater than the defined threshold duration for detection of short PR intervals. If not, the device simply returns to point A (508) of FIG. 4, and continues the test providing conditions for test initiation have remained unchanged. If the device determines that the preceding PR interval is greater than the defined threshold, it increments a count of long PR intervals at 544 and checks at 546 to determine whether the count of long PR intervals exceeds a programmed value "Z", which may be, for example, one to ten. If the long PR interval equals or exceeds the value of "Z", the device records information with regard to the test at 536 and terminates the test at 540. If not, the device returns to point A at 508, and continues to test, presuming that conditions for initiating the test remain unchanged.

What is claimed is:

1. A method of determining the occurrence of a mis-location of an atrial electrode in a cardiac stimulation system of the type comprising a an atrial pulse generator coupled with the atrial electrode and a ventricular sense amplifier coupled to a ventricular electrode, comprising:

defining a threshold PR interval;

defining a threshold number of short PR intervals;

operating the cardiac stimulation system to pace the atrium in a first pacing mode by employing the atrial pulse generator to provide atrial pacing pulses to the atrial electrode at a first energy level;

subsequently employing the atrial pulse generator to provide higher energy atrial pacing pulses to the atrial electrode at a second, greater energy level;

employing the ventricular sense amplifier to sense ventricular depolarizations following higher energy atrial pacing pulses;

measuring PR intervals between higher energy atrial pacing pulses following sensed ventricular depolarizations;

comparing measured PR intervals to the threshold PR interval to identify short PR intervals; and determining that the atrial electrode is mis-located responsive to occurrence of the threshold number of short PR intervals.

2. A method of determining the occurrence of a mis-location of an atrial electrode in a cardiac stimulation system of the type comprising a an atrial pulse generator coupled with the atrial electrode and a ventricular sense amplifier coupled to a ventricular electrode, comprising:

defining a threshold PR interval;

defining a threshold number of long PR intervals;

operating the cardiac stimulation system to pace the atrium in a first pacing mode by employing the atrial pulse generator to provide atrial pacing pulses to the atrial electrode at a first energy level;

subsequently employing the atrial pulse generator to provide higher energy atrial pacing pulses to the atrial electrode at a second, greater energy level;

employing the ventricular sense amplifier to sense ventricular depolarizations following higher energy atrial pacing pulses;

measuring PR intervals between higher energy atrial pacing pulses and following sensed ventricular depolarizations;

comparing measured PR intervals to the threshold PR interval to identify long PR intervals; and determining that the atrial electrode is at an appropriate location in the right atrium responsive to occurrence of the threshold number of long PR intervals.

3. A method of determining the occurrence of a mis-location of an atrial electrode in a cardiac stimulation system of the type comprising a an atrial pulse generator coupled with the atrial electrode and a ventricular sense amplifier coupled to a ventricular electrode, comprising:

defining a threshold PR interval;

defining a maximum number of ventricular depolarizations;

defining a threshold number of short PR intervals;

operating the cardiac stimulation system to pace the atrium in a first pacing mode by employing the atrial pulse generator to provide atrial pacing pulses to the atrial electrode at a first energy level;

subsequently employing the atrial pulse generator to provide higher energy atrial pacing pulses to the atrial electrode at a second, greater energy level;

employing the ventricular sense amplifier to sense ventricular depolarizations following higher energy atrial pacing pulses;

measuring PR intervals between higher energy atrial pacing pulses and following sensed ventricular depolarizations;

comparing measured PR intervals to the threshold PR interval to identify short PR intervals; and determining that the atrial electrode is in an appropriate location in contact with the right atrium responsive to occurrence of the maximum number of ventricular depolarizations while higher energy level pacing pulses are provided to the atrium in conjunction with occurrence of less than the threshold number of short PR intervals.

4. A method of determining the occurrence of a mis-location of an atrial electrode in a cardiac stimulation system of the type comprising a an atrial pulse generator coupled with the atrial electrode and a ventricular sense amplifier coupled to a ventricular electrode, comprising:

defining a threshold PR interval;

defining a maximum number of ventricular depolarizations;

defining a threshold number of short PR intervals;

operating the cardiac stimulation system to pace the atrium in a first pacing mode by employing the atrial pulse generator to provide atrial pacing pulses to the atrial electrode at a first energy level;

subsequently employing the atrial pulse generator to provide higher energy atrial pacing pulses to the atrial electrode at a second, greater energy level;

employing the ventricular sense amplifier to sense ventricular depolarizations following higher energy atrial pacing pulses;

measuring PR intervals between higher energy atrial pacing pulses and following sensed ventricular depolarizations;

comparing measured PR intervals to the threshold PR interval to identify short PR intervals; and determining that the atrial electrode is mis-located responsive to the threshold number of short PR intervals prior to occurrence of the maximum number of ventricular depolarizations while higher energy level pacing pulses are provided to the atrium.

5. A method of determining the occurrence of a mis-location of an atrial electrode in a cardiac stimulation system of the type comprising a an atrial pulse generator coupled with the atrial electrode and a ventricular sense amplifier coupled to a ventricular electrode, comprising:

defining a threshold PR interval;

defining a maximum number of ventricular depolarizations;

defining a threshold number of short PR intervals;

operating the cardiac stimulation system to pace the atrium in a first pacing mode by employing the atrial pulse generator to provide atrial pacing pulses to the atrial electrode at a first energy level;

subsequently employing the atrial pulse generator to provide higher energy atrial pacing pulses to the atrial electrode at a second, greater energy level;

employing the ventricular sense amplifier to sense ventricular depolarizations following higher energy atrial pacing pulses;

measuring PR intervals between higher energy atrial pacing pulses and following sensed ventricular depolarizations;

comparing measured PR intervals to the threshold PR interval to identify short PR intervals;

terminating the provision of higher amplitude pacing pulses responsive to occurrence of the threshold number of short PR intervals; and determining that the atrial electrode is appropriately located in contact with the right atrium responsive to occurrence of the maximum number of ventricular depolarizations while higher energy level pacing pulses are provided.

6. A method of determining the occurrence of a mis-location of an atrial electrode in a cardiac stimulation system of the type comprising a an atrial pulse generator and an atrial sense amplifier coupled to the atrial electrode and a ventricular sense amplifier coupled to a ventricular electrode, comprising:

determining whether an atrial tachyarrhythmia is underway based upon sensed atrial depolarizations;

defining a threshold PR interval;

defining a threshold number of short PR intervals; and responsive to a determination that atrial tachyarrhythmia is not underway, operating the cardiac stimulation system in a test mode to determine whether the atrial electrode is dislodged, the test mode comprising:

employing the atrial pulse generator to provide atrial pacing pulses to the atrial electrode;

employing the ventricular sense amplifier to sense ventricular depolarizations following atrial pacing pulses;

measuring PR intervals between atrial pacing pulses and following sensed ventricular depolarizations;

comparing measured PR intervals to the threshold PR interval to identify short PR intervals;

determining that the atrial electrode is in no longer in contact with the right atrium responsive to occurrence of the threshold number of short PR intervals.

7. A method of determining the occurrence of a dislocation of an atrial electrode in a cardiac stimulation system of the type comprising a an atrial pulse generator and an atrial sense amplifier coupled to the atrial electrode and a ventricular sense amplifier coupled to a ventricular electrode, comprising:

determining whether an atrial tachyarrhythmia is underway based upon sensed atrial depolarizations;

defining a threshold PR interval;

defining a threshold number of long PR intervals; and responsive to a determination that atrial tachyarrhythmia is not underway, operating the cardiac stimulation system in a test mode to determine whether the atrial electrode is dislodged, the test mode comprising:

employing the atrial pulse generator to provide atrial pacing pulses to the atrial electrode;

employing the ventricular sense amplifier to sense ventricular depolarizations following atrial pacing pulses;

measuring PR intervals between atrial pacing pulses and following sensed ventricular depolarizations;

comparing measured PR intervals to the threshold PR interval to identify long PR intervals; and determining that the atrial electrode is at an appropriate location in contact with the right atrium responsive to occurrence of the threshold number of long PR intervals.

8. A method according to claim 6 or claim 7 further comprising terminating operation of the system in the test mode responsive to occurrence of atrial tachyarrhythmia.

9. A cardiac stimulation system, comprising:

an atrial electrode;

an atrial pulse generator providing atrial pacing pulses, coupled to the atrial electrode;

means for sensing ventricular depolarizations;

means for defining a threshold PR interval;

means for defining a threshold number of short PR intervals;

control means for employing the atrial pulse generator to provide atrial pacing pulses to the atrial electrode at a first energy level and subsequently employing the atrial pulse generator to provide higher energy atrial pacing pulses to the atrial electrode at a second, greater energy level;

means for measuring PR intervals between the higher energy atrial pacing pulses and following sensed ventricular depolarizations;

means for comparing measured PR intervals to the threshold PR interval to identify short PR intervals; and means for determining that the atrial electrode is mislocated responsive to occurrence of the threshold number of short PR intervals.

10. A cardiac stimulation system, comprising:

an atrial electrode;

an atrial pulse generator providing atrial pacing pulses, coupled to the atrial electrode;

means for sensing ventricular depolarizations;

means for defining a threshold PR interval;

means for defining a threshold number of long PR intervals;

control means for employing the atrial pulse generator to provide atrial pacing pulses at a first energy level and subsequently employing the atrial pulse generator to provide higher energy atrial pacing pulses at a second, greater energy level;

means for measuring PR intervals between the higher energy atrial pacing pulses and following sensed ventricular depolarizations;

means for comparing measured PR intervals to the threshold PR interval to identify short PR intervals; and means for determining that the atrial electrode is at an appropriate location responsive to occurrence of the threshold number of long PR intervals.

11. A cardiac stimulation system, comprising:

an atrial electrode;

an atrial pulse generator providing atrial pacing pulses, coupled to the atrial electrode;

means for sensing ventricular depolarizations;

means for defining a threshold PR interval;

means for defining a maximum number of ventricular depolarizations;

means for defining a threshold number of short PR intervals;

control means for employing the atrial pulse generator to provide atrial pacing pulses at a first energy level and subsequently employing the atrial pulse generator to provide higher energy atrial pacing pulses at a second, greater energy level;

means for measuring PR intervals between the higher energy atrial pacing pulses and following sensed ventricular depolarizations;

means for comparing measured PR intervals to the threshold PR interval to identify short PR intervals; and means for determining that the atrial electrode is in an appropriate location responsive to occurrence of the maximum number of ventricular depolarizations while higher energy level pacing pulses are provided to the atrium in conjunction with occurrence of less than the threshold number of short PR intervals.

12. A cardiac stimulation system, comprising:

an atrial electrode;

an atrial pulse generator providing atrial pacing pulses, coupled to the atrial electrode;

means for sensing ventricular depolarizations;

means for defining a threshold PR interval;

means for defining a maximum number of ventricular depolarizations;

means for defining a threshold number of short PR intervals;

control means for employing the atrial pulse generator to provide atrial pacing pulses at a first energy level and subsequently employing the atrial pulse generator to provide higher energy atrial pacing pulses at a second, greater energy level;

means for measuring PR intervals between the higher energy atrial pacing pulses and following sensed ventricular depolarizations;

means for comparing measured PR intervals to the threshold PR interval to identify short PR intervals; and means for determining that the atrial electrode is mislocated responsive to the threshold number of short PR intervals prior to occurrence of the maximum number of ventricular depolarizations while higher energy level pacing pulses are provided to the atrium.

13. A cardiac stimulation system, comprising:

an atrial electrode;

an atrial pulse generator providing atrial pacing pulses, coupled to the atrial electrode;

means for sensing ventricular depolarizations;

means for defining a threshold PR interval;

means for defining a maximum number of ventricular depolarizations;

means for defining a threshold number of short PR intervals;

control means for employing the atrial pulse generator to provide atrial pacing pulses at a first energy level and subsequently employing the atrial pulse generator to provide higher energy atrial pacing pulses at a second, greater energy level;

means for measuring PR intervals between the higher energy atrial pacing pulses and following sensed ventricular depolarizations;

means for comparing measured PR intervals to the threshold PR interval to identify short PR intervals means for terminating the provision of higher amplitude pacing pulses responsive to occurrence of the threshold number of short PR intervals; and means for determining that the atrial electrode is appropriately located responsive to occurrence of the maximum number of ventricular depolarizations while higher energy level pacing pulses are provided.

14. A cardiac stimulation system, comprising:

an atrial electrode;

an atrial pulse generator providing atrial pacing pulses, coupled to the atrial electrode;

means for sensing ventricular depolarizations;

means for defining a threshold PR interval;

means for defining a threshold number of short PR intervals;

means for determining whether an atrial tachyarrhythmia is underway;

means responsive to a determination that atrial tachyarrhythmia is not underway for operating the cardiac stimulation system in a test mode to determine whether the atrial electrode is dislodged, the test mode comprising employing the atrial pulse generator to provide atrial pacing pulses;

means for measuring PR intervals between atrial pacing pulses provided during the test mode and following sensed ventricular depolarizations;

means for comparing measured PR intervals to the threshold PR interval to identify short PR intervals means for determining that the atrial electrode is mislocated responsive to occurrence of the threshold number of short PR intervals.

15. A cardiac stimulation system, comprising:

an atrial electrode;

an atrial pulse generator providing atrial pacing pulses, coupled to the atrial electrode;

means for sensing ventricular depolarizations;

means for defining a threshold PR interval;

means for defining a threshold number of long PR intervals;

means for determining whether an atrial tachyarrhythmia is underway;

means responsive to a determination that atrial tachyarrhythmia is not underway for operating the cardiac stimulation system in a test mode to determine whether the atrial electrode is dislodged, the test mode comprising employing the atrial pulse generator to provide atrial pacing pulses;

means for measuring PR intervals between atrial pacing pulses provided during the test mode and following sensed ventricular depolarizations;

means for comparing measured PR intervals to the threshold PR interval to identify long PR intervals means for determining that the atrial electrode is at an appropriate location responsive to occurrence of the threshold number of long PR intervals.

16. A device according to claim 14 or claim 15 further comprising means for terminating operation of the system in the test mode responsive to a determination that an atrial tachyarrhythmia is underway.

* * * * *